US008152859B2

(12) United States Patent
Balakrishnan et al.

(10) Patent No.: US 8,152,859 B2
(45) Date of Patent: Apr. 10, 2012

(54) COLOURING OF KERATINOUS FIBERS USING A PRETREATMENT COMPRISING AN IRON SALT AND A COLOUR DEVELOPER COMPRISING HYDROLYSABLE TANNIN

(75) Inventors: Lalitha Balakrishnan, Bangalore (IN); Indu Mani, Bangalore (IN); Vijay Mukund Naik, Mumbai (IN); Janhavi Sanjay Raut, Bangalore (IN); Georgios Tetradis-Mairis, Sharnbrook (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/131,606

(22) PCT Filed: Nov. 6, 2009

(86) PCT No.: PCT/EP2009/064768
§ 371 (c)(1),
(2), (4) Date: Jul. 12, 2011

(87) PCT Pub. No.: WO2010/063533
PCT Pub. Date: Jun. 10, 2010

(65) Prior Publication Data
US 2011/0253163 A1 Oct. 20, 2011

(30) Foreign Application Priority Data
Dec. 5, 2008 (IN) .......................... 2546/MUM/2008

(51) Int. Cl.
*A61Q 5/10* (2006.01)
(52) U.S. Cl. ............. 8/405; 8/404; 8/542; 8/595; 8/623; 132/202; 132/208
(58) Field of Classification Search .............. 8/405, 404, 8/542, 595, 623
See application file for complete search history.

(56) References Cited

U.S. PATENT DOCUMENTS

| 3,632,295 | A | 1/1972 | Hall et al. |
| 4,946,472 | A | 8/1990 | Motono |
| 6,248,314 | B1 | 6/2001 | Nakashimada et al. |

FOREIGN PATENT DOCUMENTS

| EP | 0327345 | | 8/1989 |
| EP | 0394930 | | 12/1990 |
| FR | 0384445 | | 11/1907 |
| FR | 1135232 | | 4/1957 |
| IN | 222788 | * | 5/2004 |
| IN | 222788 | | 9/2008 |
| JP | 49036838 | | 4/1974 |
| JP | 55154912 | | 12/1980 |
| JP | 62116504 | | 11/1985 |
| JP | 04208214 | A | 7/1992 |
| JP | 2000143683 | | 5/2000 |

OTHER PUBLICATIONS

PCT International Search Report in PCT Application PCT/EP2009/064768, dated Apr. 21, 2010.
PCT International Written Opinion in PCT Application PCT/EP2009/064768.
EP Search Report in EP Application EP 09 15 2000, dated Aug. 6, 2009.

* cited by examiner

*Primary Examiner* — Eisa Elhilo
(74) *Attorney, Agent, or Firm* — Ronald A. Koatz

(57) ABSTRACT

A method of coloring keratinous fibers comprising contacting the keratinous fibers sequentially with a pre-treatment composition and a color developer wherein: i. the pre-treatment composition comprises: (a) 0.5-25% by weight of an iron salt at a pH below 2 including 0.5-5% by weight of a reducing agent (b) a buffer effective in the pH range 3-6 and (c) a penetration enhancer comprising one or more solvents having Hansen solubility parameter δh between 1-10 $(MPa)^{1/2}$ and δp between 10-25 $(MPa)^{1/2}$ wherein the component (b) is mixed with (a) or (c) not more than 360 minutes prior to contacting the keratinous fibers and ii. the color developer is selected from one or more of hydrolysable tannin or its breakdown products or derivatives or a mixture thereof obtained from a natural or synthetic source, where the sequence of contact is in any order.

13 Claims, No Drawings

COLOURING OF KERATINOUS FIBERS USING A PRETREATMENT COMPRISING AN IRON SALT AND A COLOUR DEVELOPER COMPRISING HYDROLYSABLE TANNIN

TECHNICAL FIELD

The present invention relates to a method and a kit for enhancing the colour change of keratinous fibers especially human hair.

BACKGROUND AND PRIOR ART

Any discussion of the prior art throughout the specification should in no way be considered as an admission that such prior art is widely known or forms part of the common general knowledge in the field.

Presently the number of people wishing to have their hair coloured has increased. In order to obtain a uniform colour over the hair, permanent hair colours are used more often than temporary and semi-permanent hair colours. These types of temporary and semi-permanent hair colour do not give any control to the consumer over the amount of colour deposited. Hence most people prefer the permanent hair colours.

There are several permanent hair colouring compositions which generally come in two parts: a dye solution and a developer solution. These are generally synthetic chemicals and have a damaging effect on the hair. Each colouring application causes damage to the hair, and that damage is cumulative. Use of these dyes can also cause allergenic reactions in some people in addition to damage to structure of hair fiber.

In view of the fact that it would be desirable to develop a hair colouring composition and method that minimizes the damage caused to hair by the colouring method, there have been several attempts to permanently colour hair using black colour that is generated by using tannin and an iron salt.

It is also known in literature to use a two step method as a hair darkening system ((EP0394930, Kao, 1990), (JP04208214, Seihou Kikaku K K, 1992) and (EP0327345, Beecham, 1989)).

It is also known to pre-treat hair with a ferrous salt at a pH 3-6, in order to make the subsequent step of bleaching hair with hydrogen peroxide less damaging to hair and less irritating to skin. This invention also deals with the subsequent dyeing of hair with a colourant such as tannic acid or gallic acid which would react with iron to give the colour.

IN222788 (Hindustan Unilever Limited, 2004) discloses a method of colouring keratinous fibers by contacting the keratinous fibers sequentially with a solution/suspension of a ferric salt at pH below 3 and a colour developer selected from hydrolysable tannin or its breakdown products or derivatives or a mixture thereof obtained from a natural or synthetic source, where the sequence of contact is in any order.

It has now been found that contacting the keratinous fibers with an iron salt at pH below 2 including a reducing agent significantly enhances delivery of iron and combining it with a buffer effective in the pH range 3-6 for not more than 360 minutes prior to application and in presence of a penetration enhancer enhances the colour development that is effected by the application of the hydrolysable tannin and/or its breakdown products or derivatives. We have thus identified a superior delivery system for enhancing colour development of keratinous fibers which has not been disclosed in any of the prior art.

It is an object of the present invention to develop a method of colouring keratinous fibers that enhances the colouring effect.

It is another object of the present invention to develop a novel, stable, safe and inexpensive method of colouring keratinous fibers that enhances the colouring effect.

It is yet another object of the present invention to provide a colouring system for implementing the colouring method by providing the various components and instructions to use in the form of a kit.

DESCRIPTION OF THE INVENTION

According to the first aspect of the present invention there is provided a method of colouring keratinous fibers comprising contacting the keratinous fibers sequentially with a pre-treatment composition and a colour developer wherein:
i. the pre-treatment composition comprises:
   (a) 0.5-25% by weight of an iron salt at a pH below 2 including 0.5-5% by weight of a reducing agent;
   (b) a buffer effective in the pH range 3-6 and
   (c) a penetration enhancer comprising one or more solvents having Hansen solubility parameter $\delta h$ between 1-10 $(MPa)^{1/2}$ and $\delta p$ between 10-25 $(MPa)^{1/2}$ wherein the component (b) is mixed with (a) or (c) not more than 360 minutes prior to contacting the keratinous fibers and
ii. the colour developer is selected from one or more of hydrolysable tannin or its breakdown products or derivatives or a mixture thereof obtained from a natural or synthetic source,
where the sequence of contact is in any order.

According to another aspect of the present invention there is provided a kit for implementing the method of the invention comprising:
i. the pre-treatment composition that comprises:
   (a) a solution/suspension comprising 0.5-25% by weight of an iron salt at a pH below 2 including 0.5-5% by weight of a reducing agent
   (b) a buffer effective in the pH range 3-6 and
   (c) a penetration enhancer comprising one or more solvents having Hansen solubility parameter $\delta h$ between 1-10 $(MPa)^{1/2}$ and $\delta p$ between 10-25 $(MPa)^{1/2}$ wherein (a), (b), (c) are kept spatially separated;
ii. the colour developer selected from hydrolysable tannin or its breakdown products or derivatives or a mixture thereof obtained from a natural or synthetic source;
iii. an instruction manual It is particularly preferred that the keratinous fibers are washed between the two contacting steps. It is further preferred that the keratinous fibers are dried after washing.

The delivery of iron solution is particularly enhanced by a solvent system having Hansen solubility parameter $\delta h$ between 1-10 and $\delta p$ between 10-25 and optionally along with a solvent having Hansen solubility parameters $\delta h$ between 10-30 and $\delta p$ between 5-15. The units for Hansen solubility parameter $\delta h$ and $\delta p$ reported in all places in this document is $(MPa)^{1/2}$.

The solubility parameter has been defined as the square root of the cohesive energy density and describes the attractive strength between molecules of the material. Hansen assumed that the cohesive energy arises from the dispersive, permanent dipole-dipole interactions and hydrogen bonding forces and $\delta p$=polar term and $\delta h$=hydrogen bonding term. The data on solubility reported here were obtained from Brandrup, J. and Immergut, E. H., eds., Polymer Handbook, 3rd ed., John Wiley & Sons, New York, 1989.

DETAILED DESCRIPTION OF THE INVENTION

The present invention relates to a method of colouring the keratinous fibers by enhancing the colour development that is effected by the application of the hydrolysable tannin and/or its breakdown products or derivatives by providing the iron salt at pH below 2 including a reducing agent and penetration enhancer in presence of a buffer effective in the pH range 3-6 where the buffer is not mixed with the iron salt, reducing agent and penetration enhancer for more than 360 minutes prior to application.

The colouring system of the invention can be suitably supplied in the form of a combination kit.

The various preferred features for the method of colouring the keratinous fibers and packaging the ingredients for implementing the method of the invention in the form of a combination kit are detailed below.

Pre-Treatment Composition:

The pre-treatment composition comprises an iron salt at pH below 2 including a reducing agent, a buffer solution effective in the pH range 3-6 and a penetration enhancer. The three components are mixed for a time period not more than 360 minutes prior to contacting the keratinous fibers. It is preferable to mix them 60 minutes prior and more preferable to mix them 30 minutes prior to application. Most beneficial effects are obtained when the pre-treatment composition is applied on to the keratinous fibers immediately after mixing of the components.

Iron Salt:

The iron salt is a water soluble salt of iron. It is preferable to provide the iron salt either in the ferric or ferrous form and maintained at pH below 2 prior to mixing with the other ingredients used for pre-treating the hair. The salt is preferably ferrous or ferric chloride. The iron salt is in the range 0.5-25% by weight and preferably 1-10% and more preferably 2-6% by weight of the pre-treatment composition.

Reducing Agent:

Reducing agent group having a standard reduction potential less than −0.4 V and more preferably less than −0.77 V is used along with the iron salt for enhanced colour development. The reducing agent is incorporated in the range of 0.5-5% and more preferably in the range of 0.5-2% in the solution/suspension of the iron salt. The reducing agent is preferably selected from one or more of sulphite, metabisulphite, thiosulphate, or dithionite of sodium, ammonium, potassium or calcium, or sodium borohydrite, or lithium or aluminium hydride. Most preferably it is sodium sulphite, sodium metabisulphite, sodium thiosulphate, sodium dithionite or a mixture thereof.

Buffer:

Appropriate buffers would be ones with pKa values in the range 3-6. The preferred buffers include malate buffer, succinate buffer, acetate buffer, propionate buffer and maleate buffer. The buffer is preferably added at 0.5-25% by weight of the pre-treatment composition and more preferably at 1-10% by weight and most preferably at 2-6% by weight of the pre-treatment composition.

Penetration Enhancer:

The delivery of iron solution is particularly enhanced by incorporating a penetration enhancer that is a solvent having Hansen solubility parameter δh between 1-10 and δp between 10-25 and optionally along with a solvent having Hansen solubility parameters δh between 10-30 and δp between 5-15.

Solvent having Hansen solubility parameter δh between 1-10 and δp between 10-25 is preferably selected from carbonate derivatives of vicinal diols e.g. ethylene carbonate or propylene carbonate, acetonitrile. The penetration enhancer is incorporated at 5-50% by weight of the pre-treatment composition and preferably at 15-25% by weight of the pre-treatment composition.

The delivery of iron is further enhanced by incorporating a solvent having Hansen solubility parameter δh between 10-30 and δp between 5-15 which is preferably selected from alcohols with up to 4 carbon atoms for e.g. methanol, ethanol, propanol, butanol or their isomers; vicinal diols such as ethylene or propylene glycols. The secondary penetration enhancer is preferably incorporated at 1-20% by weight of the pre-treatment composition and more preferably at 5-15% by weight of the pre-treatment composition.

Colour Developer:

The source of colour developer is a hydrolysable tannin or its breakdown products or derivatives or a mixture thereof from a natural or synthetic source.

The hydrolysable tannins suitable for the present invention are selected from gallic acid, tannic acid, catechins and polyphenols. The natural source of hydrolysable tannins is from gall nuts, *Terminalia* species e.g. *chebula, bellerica, arjuna* etc, tea, *Mucuna pruriens* and other gallic acid rich sources. When the source of the hydrolysable tannin is from a natural source the extracts of the leaves, stem, seeds, flowers and/or fruits of the plant can be used for the purposes of the invention.

The extract of the raw and dried material can be obtained by methods generally known to obtain an extract from a plant. Especially preferred are the seeds and leaves. It is preferred to use a non-alcoholic extract and preferably an aqueous extract.

It is preferred that the hydrolysable tannin is selected from methyl gallate, ethyl gallate, gallic acid or a mixture thereof. It is further preferred that the hydrolysable tannin is methyl gallate or gallic acid.

By breakdown products is meant any break down product of a hydrolysable tannin that contains the gallic acid (1-carboxyl-3,4,5-trihydroxybenzene) substructure, or derivatives and mixtures thereof.

It is not essential to remove the solvent used for extraction. However, it is possible to completely remove the solvent by conventional methods used in the art and use the concentrated extract so obtained, especially when an alcohol is used for extraction.

The level at which the hydrolysable tannins are incorporated is in the range 0.01-40%.

Product Form:

Examples of suitable product forms include solutions, emulsions, microemulsions, gels, creams, sprays and lotions.

Other conventional ingredients such as surfactants, gelling/thickening agents, emollients, humectants, perfumes and preservatives may be incorporated to formulate the composition as desired.

Method of Application on Hair:

The present invention also relates to a method of colouring hair by a sequential treatment with the two component system that has been described. By sequential treatment is meant that the components are applied one after the other in any specific sequence. However, the preferred sequence is the application of the pre-treatment composition first followed by application of the colour developer comprising hydrolysable tannin and/or its breakdown products or derivatives. After the application of the solution of the pre-treatment composition the hair is preferably washed with water or shampoo or any suitable composition and preferably dried.

It is preferred that the component system is presented as a kit with clear instructions for the application of the kit components.

It is preferable that each component is applied once, though repeated application is possible. While a single application of the components is sufficient for colouring, in a preferred embodiment, the entire method could be repeated till the desired level of colour is obtained.

The hair colouring achieved by the present method is permanent in nature. By permanent is meant that the colour will not be removed by water or conventional surfactants. The above method of darkening hair can achieve a dark shade of black.

The Kit:

The kit used in the present invention is a container selected from paper, wood and/or plastic packaging or metal plastic strips in which the individual ingredients, the iron salt comprising the reducing agent, the buffer and the penetration enhancer and colour developer comprising the hydrolysable tannin and/or its breakdown products or derivatives are packed separately. The instruction in the form of printed information is provided on the packaging or on the strip or pouch containing the ingredients or as a separate leaflet. The instructions are in national or any local or regional language.

Optionally, an applicator for supplying the solution may also be present in the kit. A pair of gloves suitable for use when applying the solutions may also be provided with the kit.

Applicator:

Suitable applicators to enable application of the iron salt comprising the reducing agent, the buffer and the penetration enhancer are kept spatially separated during storage and enable blending just prior to application can be designed. The colour developer comprising the hydrolysable tannin and/or its breakdown products or derivatives are packed separately and applied.

The invention is further illustrated by the following non-limiting examples, in which parts and percentages are by weight unless otherwise specified.

EXAMPLES

The materials and their source used in the pre-treatment and the Colour developer composition are as follows.

Pre-Treatment Composition:
Ferrous chloride: Aldrich
Sodium dithionite: Loba Chemie, Analytical
(Reducing agent)
Propionate Buffer: Propionic acid (LOBA Chemie)
  Potassium Hydroxide (Ranbaxy)
  To obtain 100 ml of 1.5 M propionate buffer 50 ml of 6M propionic acid and 50 ml of 3M potassium hydroxide was mixed.
Propylene Carbonate: Lancaster
(Penetration enhancer)
Colour Developer Composition:
*Terminalia chebula*: Siris Impex
(Commercially available spray dried extract)
Methyl Gallate: Meridian
Sodium sulphite: Qualigens
The Composition of the Colour Developer solution used for all examples cited below was as follows:
*Terminalia Chebula* Extract: 1 g
Methyl Gallate: 1 g
Sodium Sulphite: 0.4 g
Made up to 100 ml with deionized water.

Example 1

Demonstration of the Effect of Buffer on Colour Development

White hair switches were incubated in the following pre-treatment compositions described below for 45 minutes Sample 1: Untreated
Sample 2: With pre-treatment composition comprising—per 100 ml
 (i) Ferrous chloride—3.8 g
 (ii) Sodium dithionite—0.9 g
 (iii) Propylene Carbonate—20 g
 Made up to 100 ml using deionised water
Sample 3: With pre-treatment composition comprising—per 100 ml
 (i) Ferrous chloride—3.8 g
 (ii) Sodium dithionite—0.9 g
 (iii) Propylene carbonate—20 g
 (iv) 1.5 M Propionate buffer pH 5 (30 ml)
 Made up to 100 ml using deionised water The hair switches were then washed with shampoo, rinsed with water and dried.

The hair switches were then incubated in the colour developer solution (described above) for 30 minutes. The switches were again washed well with a shampoo, rinsed with water and dried before the colour intensity was measured using sigma scan software. The colour intensity was read on a 0-255 scale where 0 refers to black and 255 refers to white. The data for the two different pre-treatment compositions is presented below in table 1.

TABLE 1

| Treatment | Sigma scan |
|---|---|
| Sample 1 | 160 |
| Sample 2 | 140 |
| Sample 3 | 78 |

The data presented show that addition of the buffer significantly enhanced the benefit obtained in comparison to the treatment in the absence of the buffer.

Example 2

Effect of Time of Mixing the Buffer on the Colour Development

The three components of the pre-treatment composition were as follows:
(a) 3.8 g Ferrous chloride+0.9 g Sodium dithionite made up to 50 ml using deionised water
(b) 1.5 M Propionate buffer pH 5.0 (30 ml)
(c) Propylene carbonate—20 ml.
(a), (b) and (c) were mixed together and kept for different time intervals 0 mins, 60 mins, 180 mins, 360 mins and 24 hrs before the experiment was conducted.

Predominantly white hair switches were dipped in the pre-treatment compositions for 60 minutes and then washed with shampoo, rinsed with water and dried.

They were then incubated in the colour developer solution (described above) for 30 minutes. The switches were washed well with shampoo, rinsed with water and dried before the colour intensity was measured using sigma scan software. The colour intensity was read on a 0-255 scale 0 refers to black and 255 refers to white. The data is presented below in Table 2.

Sample 6: Untreated
Sample 7: Immediately after mixing
Sample 8: 60 minutes after mixing
Sample 9: 180 minutes after mixing
Sample 10: 360 minutes after mixing
Sample 11: 24 hours after mixing

TABLE 2

| Treatment | Sigma scan |
|---|---|
| Sample 6 | 128 ± 30 |
| Sample 7 | 51 ± 5 |
| Sample 8 | 62 ± 9 |
| Sample 9 | 64 ± 14 |
| Sample 10 | 74 ± 17 |
| Sample 11 | 102 ± 12 |

The data show that when the composition was applied immediately after mixing the darkest colour development was obtained, which reduced when the time period was increased.

When (a), (b) and (c) were mixed for up to 360 mins prior to application, the colour obtained was not significantly different from sample 7. However, when the mixture was used 24 hours after combining (a), (b) and (c), the colour development was somewhat reduced, albeit still acceptable.

Example 3

Effect of Nature of Iron Salt on Colour Development

Predominantly white hair switches were incubated in the pre-treatment solution comprising different iron salts (examples from EP0327345) as detailed below for 60 minutes.
Sample 12: Untreated
Sample 13: Pre-treatment Composition comprising per 100 ml
  (i) Ferrous ammonium sulphate—8.5 g
  (ii) Sodium dithionite—0.9 g
  (iii) Propylene carbonate—20 g
  (iv) 1.5 M Propionate buffer pH 5.0 (30 ml)
  Made up to 100 ml using deionised water
Sample 14: Pre-treatment Composition comprising—per 100 ml
  (i) Ferric Ammonium Sulphate—8.0 g
  (ii) Sodium dithionite—0.9 g
  (iii) Propylene carbonate—20 g
  (iv) 1.5 M Propionate buffer pH 5.0 (30 ml)
  Made up to 100 ml using deionised water
Sample 15: Pre-treatment Composition comprising—per 100 ml
  (i) Ferrous chloride—3.8 g
  (ii) Sodium dithionite—0.9 g
  (iii) Propylene carbonate—20 g
  (iv) 1.5 M Propionate buffer pH 5.0 (30 ml)
  Made up to 100 ml using deionised water The hair switches were then washed with shampoo, rinsed with water and dried and incubated in the developer solution (described above) for 30 minutes. The switches were washed well with shampoo, rinsed with water and dried. The data for the different pre-treatment solution is presented in the table below (Table 2a).

TABLE 2a

| Sample | 12 | 13 | 14 | 15 |
|---|---|---|---|---|
| Greyscale intensity | 142 | 124 | 133 | 69 |
| R | 141.5 | 82 | 88 | 88 |
| G | 181.7 | 99.5 | 105 | 53 |
| B | 197.2 | 118.6 | 120 | 70 |

In the table above, the gray scale intensity and R (red, G (green) and B (values) are on the standard 0-255 scale. On the Greyscale intensity scale, the value 0 indicates "black" and the value 255 indicates white, with all grey shades in between. On the RGB scale, 0 indicates "black" and 255 indicates or "red", "green", or "blue"; for example on the RGB scale pure 'red colour' will have a 255 value for the R (red) value, and 0 for G (green) and B (blue) values; pure "black" is represented by 0 of all of R, G and B and pure "white" by 255 for all of R, G and B.

It is noted that the grey scale intensity of sample 15 is by far the best (darkest). However, the red colour, which is for a good part responsible for brownish hair colour, is equally good in all of samples 13, 14 and 15.

The ferrous chloride thus showed better colour than ferric or ferrous ammonium sulphates.

Example 4

Storage Stability

The storage stability of the penetration enhancer in presence of iron was tested by measuring the carbon dioxide evolution which was a result of the hydrolysis of the propylene carbonate. The Pre-treatment composition comprising—per 100 ml
(i) Ferrous chloride—3.8 g
(ii) Sodium dithionite—0.9 g
(iii) Propylene Carbonate—20 g
Made up to 100 ml using deionised water The pre-treatment composition was sealed in bottles and stored in a hot oven at 42° C. The amount of carbon dioxide ($CO_2$) accumulated in the head space after different durations of storage time was measured using a $CO_2$ probe. The pH of the composition was also measured. The data is presented in Table 3.

TABLE 3

| time | % $CO_2$ | pH |
|---|---|---|
| 0 days | 0 | 2.56 |
| 7 days | 27.1 | 2.18 |
| 15 days | 48.8 | 2.14 |
| 30 days | 86.2 | 1.93 |

The data shows that the pre-treatment composition was unstable and released $CO_2$ upon storage and hence it would be required to spatially separate the two components.

Thus the present invention provides for a colouring system that meets the objects of the inventions and that is a novel, stable, safe and inexpensive colouring system and a method for colouring keratinous fibers that enhances the colouring effect.

The invention claimed is:
1. A method of colouring keratinous fibers comprising contacting the keratinous fibers sequentially with a pre-treatment composition and a colour developer wherein:
  i. the pre-treatment composition comprises:
    (a) 0.5-25% by weight of an iron salt at a pH below 2 including 0.5-5% by weight of a reducing agent
    (b) 0.5-25% by weight of a buffer with pKa value in the range 3-6 and
    (c) a penetration enhancer comprising one or more solvents having Hansen solubility parameter δh between 1-10 $(MPa)^{1/2}$ and δp between 10-25 $(MPa)^{1/2}$ wherein the components (a), (b) and (c) are mixed not more than 360 minutes prior to contacting the keratinous fibers and ii. the colour developer is selected from one or more of hydrolysable tannin or its breakdown products or derivatives or a mixture thereof obtained from a natural or synthetic source.

2. A method of colouring keratinous fibers as claimed in claim 1 wherein the iron salt is ferric or ferrous chloride or a combination thereof.

3. A method of colouring keratinous fibers as claimed in claim 1 wherein the components (a), (b) and (c) are mixed not more than 60 minutes prior to contacting the keratinous fibers.

4. A method of colouring keratinous fibers as claimed in claim 1 wherein the components (a), (b) and (c) are mixed not more than 30 minutes prior to contacting the keratinous fibers.

5. A method of colouring keratinous fibers as claimed in claim 1, wherein said reducing agent is selected from a group having a standard reduction potential less than −0.4V.

6. A method of colouring keratinous fibers as claimed in claim 5, wherein said reducing agent is selected from one or more of sodium sulphite, sodium metabisulphite, sodium thiosulphate, sodium dithionite or a mixture thereof.

7. A method of colouring keratinous fibers as claimed in claim 1, wherein said colour developer is provided as an non-alcoholic solution.

8. A method of colouring keratinous fibers as claimed in claim 1 wherein said hydrolysable tannin is selected from one or more of gallic acid, tannic acid, catechins, polyphenols and derivatives thereof.

9. A method of colouring keratinous fibers as claimed in claim 8 wherein said hydrolysable tannin is methyl gallate or gallic acid or a mixture thereof.

10. A method of colouring keratinous fibers as claimed in claim 1 wherein the natural source of said hydrolysable tannin is selected from gall nuts, *Terminalia* species e.g, *chebula, bellerica, arjuna*, tea, *Mucuna pruriens* and other gallic acid rich sources.

11. A method of colouring keratinous fibers as claimed in claim 1 wherein the keratinous fibers are washed between the two contacting steps.

12. A method of colouring keratinous fibers as claimed in claim 1, wherein said penetration enhancer comprises a second solvent system comprising one or more solvents having a Hansen solubility parameters δh between 10-30 $(MPa)^{1/2}$ and δp between 5-15 $(MPa)^{1/2}$.

13. A kit for implementing said method of colouring keratinous fibers as claimed in claim 1 comprising:
   i. a pre-treatment composition comprising:
      (a) solution/suspension comprising 0.5-25% by weight of an iron salt at a pH below 2 and 0.5-5% by weight of a reducing agent
      (b) 0.5 to 25% by weight of a buffer effective in the pH range 3-6 and
      (c) a penetration enhancer comprising one or more solvents having Hansen solubility parameter δh between 1-10 $(MPa)^{1/2}$ and δp between 10-25 $(MPa)^{1/2}$ wherein (a), (b), (c) are kept spatially separated;
   ii. a colour developer selected from hydrolysable tannin or its breakdown products or derivatives or a mixture thereof obtained from a natural or synthetic source; and
   iii. an instruction manual.

* * * * *